(12) United States Patent  (10) Patent No.: US 9,388,447 B2
Jerums et al.  (45) Date of Patent: Jul. 12, 2016

(54) METHOD FOR CULTURING MAMMALIAN CELLS TO IMPROVE RECOMBINANT PROTEIN PRODUCTION

(71) Applicant: Amgen Inc., Thousand Oaks, CA (US)

(72) Inventors: Matthew I. Jerums, Oak View, CA (US); Amanda Kano, Livermore, CA (US); Henry Lin, Fremont, CA (US); Shun Luo, Irvine, CA (US); Jian Wu, Bothell, WA (US); Rebecca E. McCoy, Seattle, WA (US); Arvia E. Morris, Seattle, WA (US)

(73) Assignee: AMGEN, INC., Thousand Oaks, CA (US)

( * ) Notice: Subject to any disclaimer, the term of this patent is extended or adjusted under 35 U.S.C. 154(b) by 0 days.

(21) Appl. No.: 14/821,574

(22) Filed: Aug. 7, 2015

(65) Prior Publication Data

US 2016/0040207 A1  Feb. 11, 2016

Related U.S. Application Data

(62) Division of application No. 14/112,202, filed as application No. PCT/US2012/034532 on Apr. 20, 2012, now Pat. No. 9,133,493.

(60) Provisional application No. 61/477,900, filed on Apr. 21, 2011, provisional application No. 61/490,981, filed on May 27, 2011.

(51) Int. Cl.
*C12N 5/077* (2010.01)
*C12P 21/00* (2006.01)
*C12N 5/00* (2006.01)

(52) U.S. Cl.
CPC .............. *C12P 21/00* (2013.01); *C12N 5/0037* (2013.01); *C12N 5/0043* (2013.01); *C12N 2500/32* (2013.01); *C12N 2510/02* (2013.01); *C12N 2511/00* (2013.01)

(58) Field of Classification Search
None
See application file for complete search history.

(56) References Cited

U.S. PATENT DOCUMENTS 5,672,502 A * 9/1997 Birch ..................... C07K 16/34
435/212

* cited by examiner

*Primary Examiner* — Jim Ketter
(74) *Attorney, Agent, or Firm* — Alex A. Andalis

(57) ABSTRACT

The present invention relates to methods for mammalian cell culture. The methods make use of independent tyrosine and cystine feed streams.

11 Claims, 24 Drawing Sheets

METHOD FOR CULTURING MAMMALIAN CELLS TO IMPROVE RECOMBINANT PROTEIN PRODUCTION

CROSS REFERENCE TO RELATED APPLICATIONS

This application is a divisional application of U.S. patent application Ser. No. 14/112,202 filed Feb. 24, 2014, which is a national stage application under 37 U.S.C. §371 of International Application No. PCT/US2012/034532 filed Apr. 20, 2012 which claims the benefit under 35 U.S.C. §119 of U.S. Provisional Application Ser. No. 61/477,900, filed Apr. 21, 2011 and U.S. Provisional Application Ser. No. 61/490,981, filed May 27, 2011, which are hereby incorporated by reference in their entirety.

FIELD OF INVENTION

The present invention relates to a method for mammalian cell culture. The method makes use of independent tyrosine and cystine feed streams.

BACKGROUND OF INVENTION

Clinical manufacture of therapeutic proteins is an expensive, large scale endeavor. Maintaining cell growth and viability throughout the cell culture process is very important. As the demand for greater quantities of therapeutic recombinant proteins increases, positive increases in protein production, cell growth and viability are sought out by implementing new methods to improve cell development, media optimization and process control parameters, and to intensify harvest and purification processes. Much effort is now being placed on process optimization, particularly methods and formulations for feeding production cell cultures. One such method is the use of a concentrated feed medium during the production phase, often used in fed batch culture processes, to improve protein titer, cell growth, and/or cell viability.

Tyrosine is a critical amino acid for sustaining cultured cells in growth and viability and is included in growth media and concentrated production media formulations. A depletion of tyrosine in a production culture can lead to decreases in cell growth, viability and/or protein production.

Due to poor solubility at neutral pH, tyrosine cannot be compounded at high concentrations in either the growth or concentrated feed medium. Therefore, only a limited amount of tyrosine can be compounded into media formulations without causing the media to precipitate. Phenylalanine can convert to tyrosine via the enzyme phenylalanine hydroxylase (PAH) in certain cell types and can also be included in media formulations.

Cysteine is another important amino acid for sustaining cultured mammalian cells. However, cysteine readily oxidizes to form cystine in neutral or slightly alkaline solutions. So while cysteine is freely soluble in water, it may contribute to insolubility and/or precipitation when in its oxidized form.

Mammalian cells are typically grown in cultures that are at or near neutral pH, such as from about pH 6.5 to about pH 7.5. Tyrosine and cysteine, necessary components of mammalian cell culture media, can cause media formulations to destabilize in the neutral conditions necessary for cell growth.

New cell culture media formulations and/or methods for feeding production cultures that provide even incremental improvements in cell growth, viability and/or protein production are valuable, given the expense of large scale cell culture processes and the difficulty and expense of building and obtaining regulatory approval for new large-scale, commercial culture facilities.

There is a continuing need to develop media formulations and feeding methods that are able to provide adequate amino acid levels in a production culture to maintain and improve cell viability, specific productivity, and titer. Any improvements to cell culture media formulations and/or feeding strategies that allow for flexibility and customization to facilitate desirable recombinant polypeptide expression, titer, cell growth and/or cell viability can lead to ease of maintenance, higher production levels, thereby reducing the costs associated with manufacturing protein therapeutics. The invention fulfills these needs by providing a simple, easy and inexpensive method of increasing cell growth and protein production.

SUMMARY OF THE INVENTION

The present invention provides a method of culturing Chinese Hamster Ovary (CHO) cells expressing a recombinant protein, comprising growing the CHO cells in a defined serum-free culture medium during a growth phase and maintaining the CHO cells in the cell culture medium during a production phase by supplementing the cell culture with a concentrated defined serum-free feed medium that does not contain tyrosine, cysteine or cystine, and further supplementing the cell culture with an independent tyrosine and cystine feed, wherein viability was prolonged, specific productivity and titer was maintained and not diminished by the independent tyrosine and cystine feed. In one embodiment the independent tyrosine and cystine feed provides at least about 0.1 mM to at least about 2.0 mM tyrosine at each feed. In a related embodiment the independent tyrosine and cystine feed provides at least about 1.38 mM tyrosine. In another embodiment the independent tyrosine and cystine feed provides at least about 0.17 mM to at least about 0.72 mM cystine at each feed. In a related embodiment the independent tyrosine and cystine feed provides at least about 0.50 mM cystine. In another embodiment the independent tyrosine and cystine feed begins at least by day 5 of the production phase. In a related embodiment the independent tyrosine and cystine feed begins on day 3 of the production phase. In another embodiment the independent tyrosine and cystine feed begins prior to the production phase. In yet another embodiment the independent tyrosine and cystine feed is made concurrently with the feed of the concentrated serum-free defined feed medium. In another embodiment the independent tyrosine and cystine feed is not concurrent with the feed of the concentrated serum-free defined feed medium. In a further embodiment the recombinant protein is selected from the group consisting of a human antibody, a humanized antibody, a chimeric antibody, a recombinant fusion protein, or a cytokine.

The invention also provides a method of culturing CHO cells expressing a recombinant protein, comprising growing the CHO cells in a defined serum-free culture medium during a growth phase and maintaining the CHO cells in the cell culture medium during a production phase by supplementing the cell culture with a concentrated serum-free defined feed medium containing tyrosine and further supplementing the cell culture with an independent tyrosine feed, wherein viability was prolonged, specific productivity was maintained, and titer was improved compared to CHO cells not receiving independent tyrosine feeds. Within one related embodiment the independent tyrosine provides at least about 1 mM and 2 mM tyrosine at each feed. In yet another related embodiment the independent tyrosine feed provides at least about 1 mM tyrosine. Within another related embodiment the concentration of tyrosine in the cell culture medium does not exceed 8 mM. In yet another related embodiment the independent tyrosine feeds begin just prior to the production phase. Within another related embodiment the independent tyrosine feeds begin on day 7. In yet another related embodiment the independent tyrosine feed is made concurrently with the feed of the concentrated serum-free defined feed medium. Within certain other related embodiments the recombinant protein is selected from the group consisting of a human antibody, a humanized antibody, a chimeric antibody, a recombinant fusion protein, or a cytokine.

DETAILED DESCRIPTION OF THE INVENTION

Figure 1A:
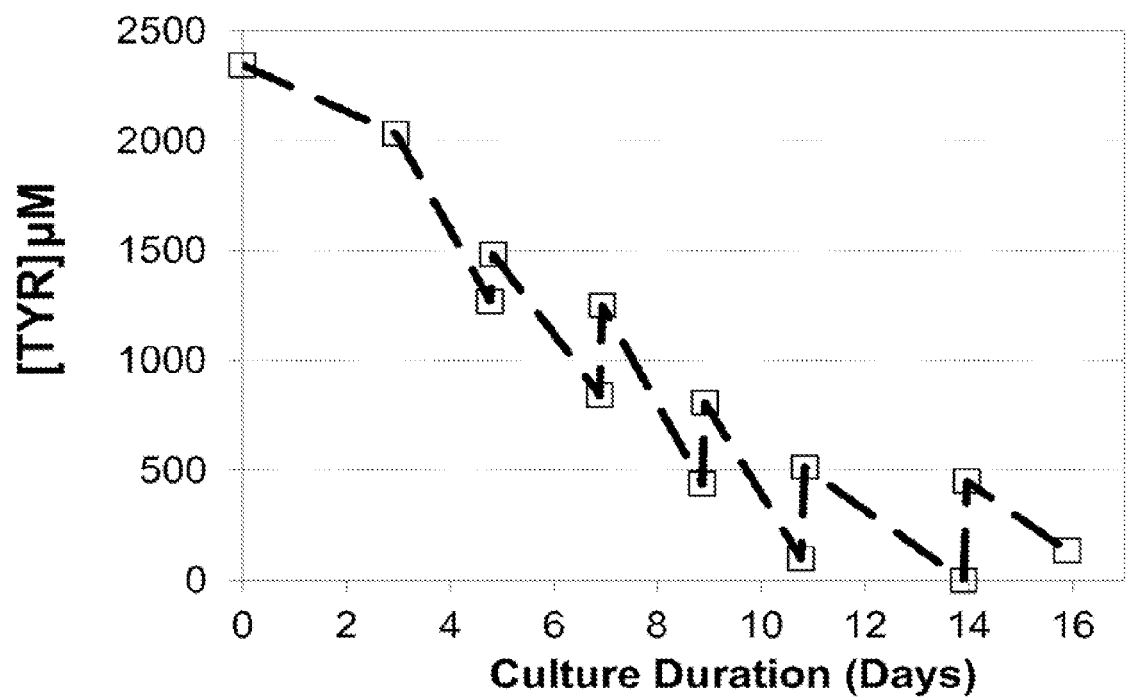
FIG. 1A is a graph showing tyrosine concentration over time.

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of". The section headings used herein are for organizational purposes only and are not to be construed as limiting the subject matter described. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). All documents, or portions of documents, cited in this application, including but not limited to patents, patent applications, articles, books, and treatises, are hereby expressly incorporated by reference.

The invention is based on the discovery that use of an independent feed of a concentrated tyrosine solution was able to overcome the depletion of tyrosine in the culture medium when the culture only received concentrated production medium feeds that contained tyrosine in addition to other amino acids such as phenylalanine as well as other nutrients. Addition of the independent tyrosine feed increased cell growth, viability and polypeptide production from a recombinantly engineered animal cell line expressing a protein of interest, compared to cultures receiving concentrated feed medium alone. Addition of the independent tyrosine feed offset the tyrosine depletion seen in cultures receiving only the concentrated feed medium and resulted in enhanced culture robustness and improved the yield of the polypeptide of interest.

The present invention provides a method of culturing Chinese Hamster Ovary (CHO) cells expressing a recombinant protein. The inventive method comprises growing the CHO cells in a defined serum-free culture medium during a growth phase followed by maintaining the CHO cells during a production phase, wherein the cell culture medium is periodically supplemented with a concentrated feed medium and is further supplemented with periodic independent tyrosine feeds, wherein viability was prolonged, specific productivity was maintained, and titer was improved compared to CHO cells not receiving independent tyrosine feeds. The concentration of tyrosine added by each independent tyrosine feed is at least about 1 mM-2 mM, preferably about 1 mM. The formulation of the concentrated feed medium contains up to about 4.5 mM tyrosine. The independent tyrosine feeds are adjusted such that the concentration of tyrosine in the culture medium does not exceed 8 mM. The independent tyrosine feeds can begin just prior to or at the start of the production phase. The independent tyrosine feed can be accomplished by fed batch to the cell culture medium on the same or different days as the concentrated feed medium. Such independent tyrosine feeds can be added to the cell culture medium after one or more days, and can also be added repeatedly during the course of the production phase, as long as tyrosine depletion in the cell culture medium is avoided. For example, the production phase can last from 7 days to as long as 8, 9, 10, 11, 12, 13, or 14 days or longer. The cell culture medium can be supplemented with the independent tyrosine feeds immediately and/or on days 2, 3, 4, 5, 6, 7, 8, 9, 10, 11, 12, 13 and/or later days of the production phase.

The invention also provides the use of an independent concentrated feed solution containing tyrosine and cystine. It was discovered that independent concentrated feed solution containing tyrosine and cystine was able to adequately supplement a mammalian cell culture receiving feeds of a concentrated feed medium that did not contain tyrosine, cysteine or cystine in its formulation. Independent feeds of the tyrosine and cystine solution maintained cell growth, viability and polypeptide production from a recombinantly engineered mammalian cell line expressing a protein of interest, without negative impact on the cell culture or the protein production. The combined cystine and tyrosine feed solution can be prepared at high pH so the feed solution has the added benefit of not requiring subsequent viral inactivating treatments such as pasteurization or viral filtration. The pH of the feed solution is at least about pH 10.0 to at least about pH 12.0. The pH of the feed solution can be 10.0, 10.5, 11.0, 11.5, 12.0 or any value in between. Preferably the pH is at least about 10.0. Removing cysteine and tyrosine from the concentrated feed medium allows for the reduction or removal of stabilizers, such as sodium pyruvate (Published US Application No. 2009/0123975), in concentrated feed medium formulations without the resulting cell culture media instability due to precipitation of cysteine and tyrosine. Independent feeds of a concentrated cystine and tyrosine feed solution did not cause precipitation in the culture medium.

The present invention provides a method of culturing Chinese Hamster Ovary (CHO) cells expressing a recombinant protein. The inventive method comprises growing the CHO cells in a defined serum-free culture medium during a growth phase followed by maintaining the CHO cells in the cell culture medium during a production phase, wherein the cell culture medium is periodically supplemented with a concentrated defined serum-free feed medium that does not contain tyrosine, cysteine or cystine in its formulation and is further supplemented with periodic independent feeds of a tyrosine and cystine feed solution, wherein viability was prolonged, specific productivity and titer was maintained and not diminished by the independent tyrosine and cystine feed. The concentration of tyrosine added by each independent tyrosine and cystine feed is at least about 0.1 mM to at least about 2.0 mM tyrosine. The concentration of tyrosine is at least about 0.1 mM, 0.5 mM, 1.0 mM, 1.25 mM, 1.3 mM, 1.5 mM, 1.75 mM, 2.0 mM or any value in between. Preferably the tyrosine concentration is at least about 1.38 mM. The concentration of cystine added by each independent tyrosine and cystine feed is at least about at least about 0.17 mM to at least about 0.72 mM. The concentration of tyrosine is at least about 0.17 mM, 0.2 mM, 0.03 mM, 0.4 mM, 0.5 mM, 0.6 mM, 0.7 mM, 0.72 mM and any value in between. Preferably the cystine concentration is at least about 0.5 mM. The independent tyrosine and cystine feed can begin prior to or at the start of the production phase. The independent tyrosine and cystine feed can be accomplished by fed batch to the cell culture medium on the same or different days as the concentrated feed medium. Such independent tyrosine and cystine feeds can be added to the cell culture medium after one or more days, and can also be added repeatedly during the course of the production phase, as long as tyrosine, cysteine and cystine depletion in the cell culture medium is avoided. For example, the production phase can last from 7 days to as long as 8, 9, 10, 11, 12, 13, or 14 days or longer. The cell culture medium can be supplemented with the independent tyrosine and cystine feed during the growth stage and/or on days 2, 3, 4, 5, 6, 7, 8, 9, 10, 11, 12, 13 or later during the production phase.

As used herein "peptide," "polypeptide" and "protein" are used interchangeably throughout and refer to a molecule comprising two or more amino acid residues joined to each other by peptide bonds. Peptides, polypeptides and proteins are also inclusive of modifications including, but not limited to, glycosylation, lipid attachment, sulfation, gamma-carboxylation of glutamic acid residues, hydroxylation and ADP-ribosylation. Polypeptides can be of scientific or commercial interest, including protein-based drugs. Polypeptides include, among other things, antibodies, fusion proteins, and cytokines. Peptides, polypeptides and proteins are produced by recombinant animal cell lines using cell culture methods and may be referred to as "recombinant peptide", "recombinant polypeptide" and "recombinant protein". The expressed protein(s) may be produced intracellularly or secreted into the culture medium from which it can be recovered and/or collected.

Examples of polypeptides that can be produced with the methods of the invention include proteins comprising amino acid sequences identical to or substantially similar to all or part of one of the following proteins: tumor necrosis factor (TNF), flt3 ligand (WO 94/28391), erythropoeitin, thrombopoeitin, calcitonin, IL-2, angiopoietin-2 (Maisonpierre et al. (1997),*Science* 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682; Rüegg and Pytela (1995), *Gene* 160:257-62) growth hormone, insulin, insulinotropin, insulin-like growth factors, parathyroid hormone, interferons including a-interferons, γ-interferon, and consensus interferons (U.S. Pat. Nos. 4,695,623 and 4,897471), nerve growth factor, brain-derived neurotrophic factor, synaptotagmin-like proteins (SLP 1-5), neurotrophin-3, glucagon, interleukins, colony stimulating factors, lymphotoxin-β, leukemia inhibitory factor, and oncostatin-M. Descriptions of proteins that can be produced according to the inventive methods may be found in, for example, *Human Cytokines: Handbook for Basic and Clinical Research, all volumes* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook*, Vols. 1 and 2 (Thompson and Lotze eds., Academic Press, San Diego, Calif., 2003).

Additionally the methods of the invention would be useful to produce proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279), Interleukin-1 (IL-1) receptors (types I and II; EP Patent No. 0460846, U.S. Pat. Nos. 4,968,607, and 5,767,064,), IL-1 receptor antagonists (U.S. Pat. No. 6,337,072), IL-1 antagonists or inhibitors (US Patent Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other proteins that can be produced using the invention include proteins comprising all or part of the amino acid sequences of differentiation antigens (referred to as CD proteins) or their ligands or proteins substantially similar to either of these. Such antigens are disclosed in *Leukocyte Typing VI* (Proceedings of the VIth International Workshop and Conference, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be produced using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

The term "antibody" includes reference to both glycosylated and non-glycosylated immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof Also included are proteins having an antigen binding fragment or region such as Fab, Fab', F(ab')$_2$, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), *Cytokine Growth Factor Rev.* 13(1): 19-25), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be produced using the methods of the invention include but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizomab, zalutumumab, and zanolimumab.

The invention can also be used to produce recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. See e.g. WO94/10308; Lovejoy et al. (1993), *Science* 259:1288-1293; Harbury et al. (1993), *Science* 262: 1401-05; Harbury et al. (1994), *Nature* 371:80-83; Håkansson et al.(1999), *Structure* 7:255-64. Specifically included among such recombinant fusion proteins are proteins in which a portion of a receptor is fused to an Fc portion of an antibody such as etanercept (a p75 TNFR:Fc), and belatacept (CTLA4:Fc).

For the purposes of this invention, cell culture medium is a media suitable for growth of animal cells, such as mammalian cells, in in vitro cell culture. Cell culture media formulations are well known in the art. Typically, cell culture media are comprised of buffers, salts, carbohydrates, amino acids, vitamins and trace essential elements. The cell culture medium may or may not contain serum, peptone, and/or proteins. Various tissue culture media, including serum-free and defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

Cell culture media may be serum-free, protein-free, and/or peptone-free. "Serum-free" applies to a cell culture medium that does not contain animal sera, such as fetal bovine serum. "Protein-free" applies to cell culture media free from exogenously added protein, such as transferrin, protein growth factors IGF-1, or insulin. Protein-free media may or may not contain peptones. "Peptone-free" applies to cell culture media which contains no exogenous protein hydrolysates such as animal and/or plant protein hydrolysates. Eliminating serum and/or hydrolysates from cell culture media has the advantage of reducing lot to lot variability and enhancing processing steps, such as filtration. However, when serum and/or peptone are removed from the cell culture media, cell growth, viability and/or protein expression may be diminished or less than optimal. As such, serum-free and/or peptone-free cell culture medium may be highly enriched for amino acids, trace elements and the like. See, for example, U.S. Pat. Nos. 5,122,469 and 5,633,162. Although there are many media formulations, there is a need to develop defined media formulations that perform as well or preferably better than those containing animal sera and/or peptones.

Defined cell culture media formulations are complex, containing amino acids, inorganic salts, carbohydrates, lipids, vitamins, buffers and trace essential elements. Identifying the components that are necessary and beneficial to maintain a cell culture with desired characteristics is an on going task. Defined basal media formulations which are supplemented or enriched to meet the needs of a particular host cell or to meet desired performance parameters is one approach to developing defined media. Identifying those components and optimum concentrations that lead to improved cell growth, viability and protein production is an ongoing task.

By cell culture or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, roller bottles, shake flasks, or stirred tank bioreactors, with or without microcarriers, and operated in a batch, fed batch, continuous, semi-continuous, or perfusion mode are available for mammalian cell culture.

Mammalian cells, such as CHO cells, may be cultured in small scale cultures, such as for example, in 100 ml containers having about 30 ml of media, 250 ml containers having about 80 to about 90 ml of media, 250 ml containers having about 150 to about 200 ml of media. Alternatively, the cultures can be large scale such as for example 1000 ml containers having about 300 to about 1000 ml of media, 3000 ml containers having about 500 ml to about 3000 ml of media, 8000 ml containers having about 2000 ml to about 8000 ml of media, and 15000 ml containers having about 4000 ml to about 15000 ml of media. Large scale cell cultures, such as for clinical manufacturing of protein therapeutics, are typically maintained for days, or even weeks, while the cells produce the desired protein(s).

During this time the culture can be supplemented with a concentrated feed medium containing components, such as nutrients and amino acids, which are consumed during the course of the production phase of the cell culture. Concentrated feed medium may be based on just about any cell culture media formulation. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount. Concentrated feed media are often used in fed batch culture processes.

Fed batch culture is a widely-practiced culture method for large scale production of proteins from mammalian cells. See e.g. Chu and Robinson (2001), Current Opin. Biotechnol. 12: 180-87. A fed batch culture of mammalian cells is one in which the culture is fed, either continuously or periodically, with a concentrated feed medium containing nutrients. Feeding can occur on a predetermined schedule of, for example, every day, once every two days, once every three days, etc. The culture can be monitored for tyrosine, cystine and/or cysteine levels in the culture medium and can be adjusted through feedings of a concentrated tyrosine or tyrosine and cystine solution so as to keep tyrosine, cysteine and/or cystine within a desired range. When compared to a batch culture, in which no feeding occurs, a fed batch culture can produce greater amounts of protein. See e.g. U.S. Pat. No. 5,672,502.

The method according to the present invention may be used to improve the production of recombinant proteins in both single phase and multiple phase culture processes. In a single phase process, cells are inoculated into a culture environment and the disclosed methods are employed during the single production phase. In a multiple stage process, cells are cultured in two or more distinct phases. For example cells may be cultured first in one or more growth phases, under environmental conditions that maximize cell proliferation and viability, then transferred to a production phase, under conditions that maximize protein production. In a commercial process for production of a protein by mammalian cells, there are commonly multiple, for example, at least about 2, 3, 4, 5, 6, 7, 8, 9, or 10 growth phases that occur in different culture vessels preceding a final production phase. The growth and production phases may be preceded by, or separated by, one or more transition phases. In multiple phase processes, the method according to the present invention can be employed at least during the production phase, although it may also be employed in a preceding growth phase. A production phase can be conducted at large scale. A large scale process can be conducted in a volume of at least about 100, 500, 1000, 2000, 3000, 5000, 7000, 8000, 10,000, 15,000, 20,000 liters. A growth phase may occur at a higher temperature than a production phase. For example, a growth phase may occur at a first temperature from about 35° C. to about 38° C., and a production phase may occur at a second temperature from about 29° C. to about 37° C., optionally from about 30° C. to about 36° C. or from about 30° C. to about 34° C. In addition, chemical inducers of protein production, such as, for example, caffeine, butyrate, and hexamethylene bisacetamide (HMBA), may be added at the same time as, before, and/or after a temperature shift. If inducers are added after a temperature shift, they can be added from one hour to five days after the temperature shift, optionally from one to two days after the temperature shift.

The invention finds particular utility in improving or maintaining cell growth, viability and/or protein production via cell culture processes. The cell lines (also referred to as "host cells") used in the invention are genetically engineered to express a polypeptide of commercial or scientific interest. Cell lines are typically derived from a lineage arising from a primary culture that can be maintained in culture for an unlimited time. Genetically engineering the cell line involves transfecting, transforming or transducing the cells with a recombinant polynucleotide molecule, and/or otherwise altering (e.g., by homologous recombination and gene activation or fusion of a recombinant cell with a non-recombinant cell) so as to cause the host cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., *Large Scale Mammalian Cell Culture*, 1990, pp. 15-69.

Animal cell lines are derived from cells whose progenitors were derived from a multi-cellular animal. One type of animal cell line is a mammalian cell line. A wide variety of mammalian cell lines suitable for growth in culture are available from the American Type Culture Collection (Manassas, Va.) and commercial vendors. Examples of cell lines commonly used in the industry include VERO, BHK, HeLa, CV1 (including Cos), MDCK, 293, 3T3, myeloma cell lines (e.g., NSO, NS1), PC12, WI38 cells, and Chinese hamster ovary (CHO) cells. CHO cells are widely used for the production of complex recombinant proteins, e.g. cytokines, clotting factors, and antibodies (Brasel et al. (1996), *Blood* 88:2004-2012; Kaufman et al. (1988), *J.Biol Chem* 263:6352-6362; McKinnon et al. (1991), *J Mol Endocrinol* 6:231-239; Wood et al. (1990), *J. Immunol.* 145:3011-3016). The dihydrofolate reductase (DHFR)-deficient mutant cell lines (Urlaub et al. (1980), *Proc Natl Acad Sci USA* 77: 4216-4220), DXB11 and DG-44, are desirable CHO host cell lines because the efficient DHFR selectable and amplifiable gene expression system allows high level recombinant protein expression in these cells (Kaufman R. J. (1990), *Meth Enzymol* 185:537-566). In addition, these cells are easy to manipulate as adherent or suspension cultures and exhibit relatively good genetic stability. CHO cells and proteins recombinantly expressed in them have been extensively characterized and have been approved for use in clinical commercial manufacturing by regulatory agencies.

The methods of the invention can be used to culture cells that express recombinant proteins of interest. The expressed recombinant proteins may be produced intracellularly or be secreted into the culture medium from which they can be recovered and/or collected. In addition, the proteins can be purified, or partially purified, from such culture or component (e.g., from culture medium or cell extracts or bodily fluid) using known processes and products available from commercial vendors. The purified proteins can then be "formulated", meaning buffer exchanged, sterilized, bulk-packaged, and/or packaged for a final user. Suitable formulations for pharmaceutical compositions include those described in *Remington's Pharmaceutical Sciences*, 18th ed. 1995, Mack Publishing Company, Easton, Pa.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Example 1

It was observed that when growing CHO cells expressing recombinant antibodies in a chemically defined media containing tyrosine, that tyrosine was depleted during the production process despite regular supplements to the culture medium with a concentrated feed medium containing tyrosine. The depletion resulted in a fast drop in viability, decrease in specific productivity (Qp) and loss of titer, which negatively impacted the production of the recombinant protein. (FIG. 1A, B, C, D). Phenylalanine accumulated in the culture medium but did not convert to tyrosine after tyrosine depletion (FIG. 1E)

Tyrosine is a poorly soluble amino acid and as such it is difficult to increase the amount of tyrosine in the concentrated feed medium beyond 4.5 mM or 1.2 g/L to meet the demands of the production culture. Phenylalanine is known to convert tyrosine via PAH but did not contribute tyrosine to the tyrosine depleted cell culture medium. In an attempt to overcome the rapid depletion of tyrosine during the production, a concentrated tyrosine solution was fed to the cell culture medium in addition to the concentrated feed medium that included tyrosine in its formulation.

CHO cells expressing a recombinant antibody were inoculated at $1\times10^6$ c/ml by centrifugation in 120 ml of a serum-free defined growth medium containing 0.6 g/L tyrosine. Cultures were maintained in vented 500 ml shake flasks and kept in a 36° C., 5% $CO_2$.

A 150 g/L tyrosine $2Na^+$ $2H_2O$ concentrated tyrosine feed solution was prepared in $dH_2O$ (SAFC Biosciences Lenexa, Kans.).

Production cultures were maintained for 16 days. Flasks were sampled (14 mls) on days 5, 7, 9, 11, 13, and 16. Cultures were fed 9% based on current volume (9-10.5 mls) of a concentrated serum-free defined feed medium containing 1.2 g/L tyrosine, up to day 13. Glucose was maintained at a range of 6-8 g/L and 1 mM tyrosine $2Na^+$ $2H_2O$ supplements (0.15-0.2 mls) using the concentrated tyrosine solution were independently added starting on day 7 or 9 and subsequent feed days. A day 0 sample and pre- and post-feed samples up to day 16 were saved for titer and amino acid analysis. A culture that did not receive the independent tyrosine feeds was included as a control and to confirm initial observations of tyrosine depletion.

Viable cell density (VCD) and viability were measured by the CEDEX (Innovatis, Germany) and metabolites by the NOVA BioProfile 100+ (NOVA Biomedical, Mass.). Values of pH, $pO_2$, and $pCO_2$ were analyzed by the Bioprofile pHox (NOVA Biomedical, Mass.) and osmolality by the model 2020 osmometer (Advanced Instruments, Norwood, Mass.). Titer was measured by reverse-phase HPLC analysis using affinity chromatography where Protein A was immobilized on a column support. At neutral pH, antibody molecules were bound to the Protein A through the Fc region while host-cell proteins, conditioned media components and buffer were eluted from the column in the flow-through. Captured antibodies were eluted at acidic pH and detected by UV absorbance at 280 nm. A calibration curve was derived from a universal antibody standard and the corresponding peak areas using linear regression analysis. Concentrations of the antibody in the test samples were then calculated from the calibration curve and the ratio of the extinction coefficients from the Universal antibody standard and the antibody tested.

Amino acid analysis was performed using an AccuTag pre-column derivatization chemistry reagent kit according to the manufacturer's instructions (Waters Corporation, Milford, Mass.)

Figure 2A:
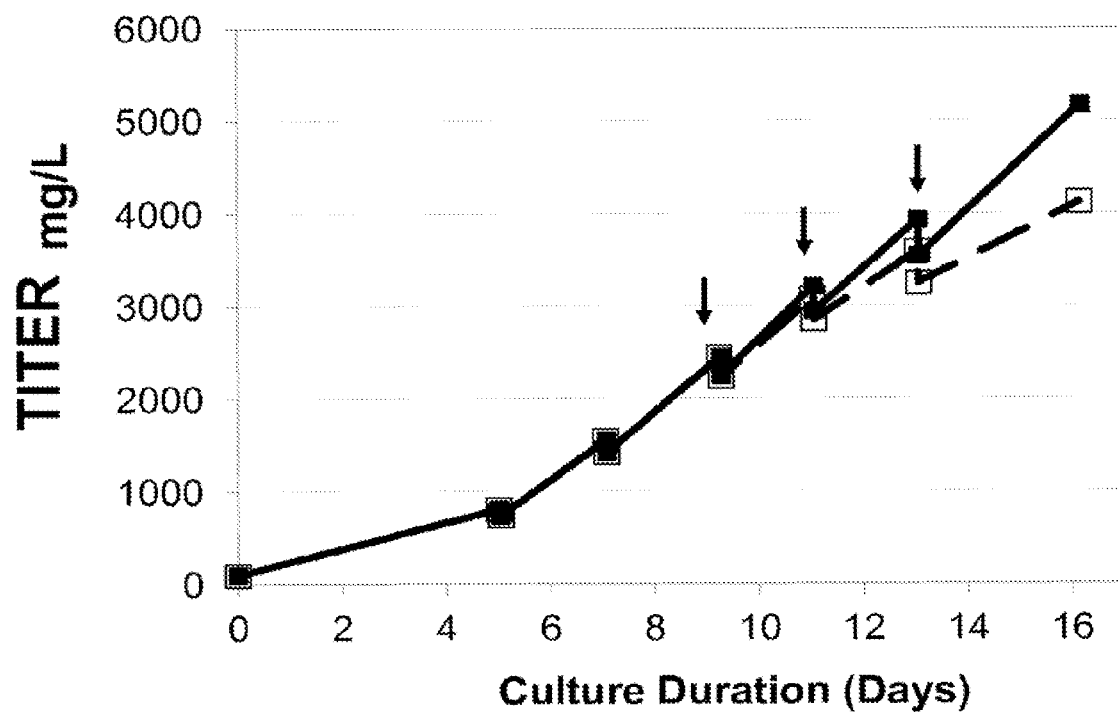
FIG. 2A is a graph showing titer over time.
Figure 2B:
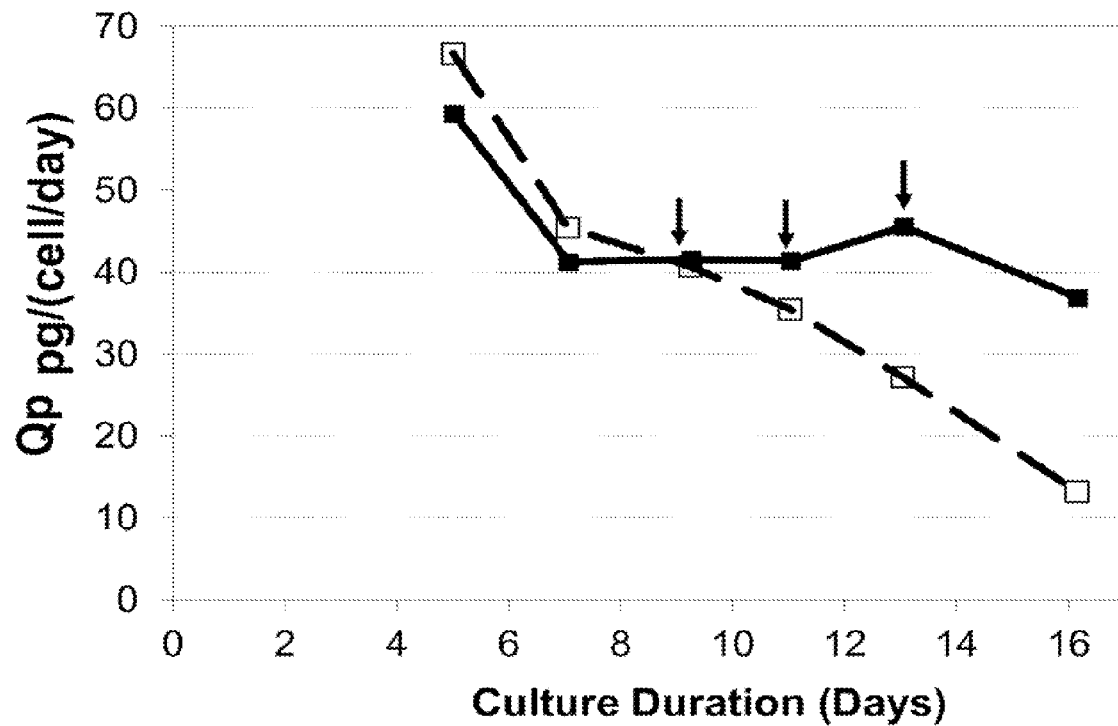
FIG. 2B is a graph showing specific productivity (Qp) over time.
Figure 2C:
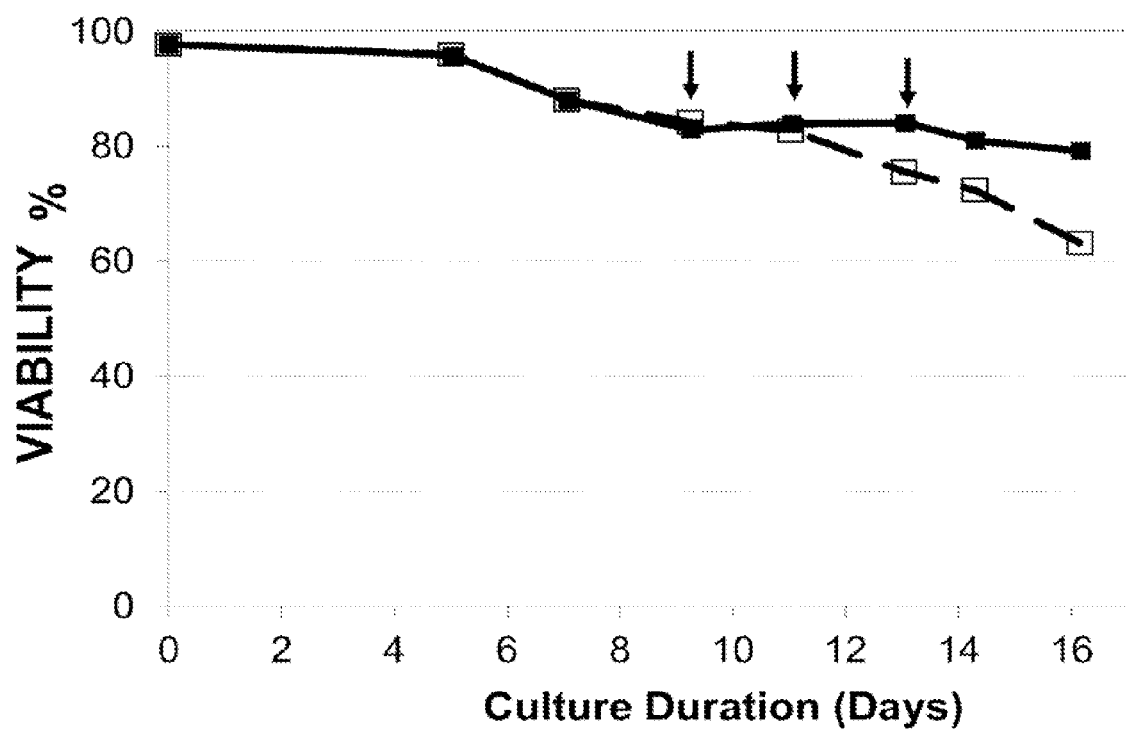
FIG. 2C is a graph showing viability over time.
Figure 2D:
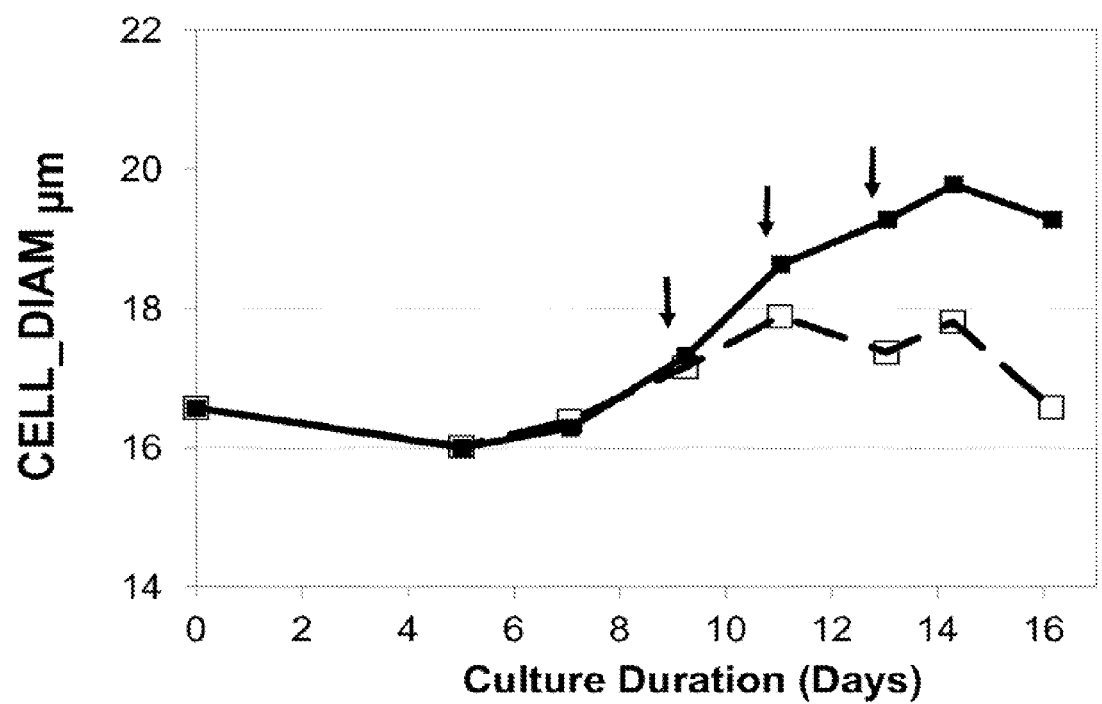
FIG. 2D is a graph showing cell diameter over time.
Figure 2E:
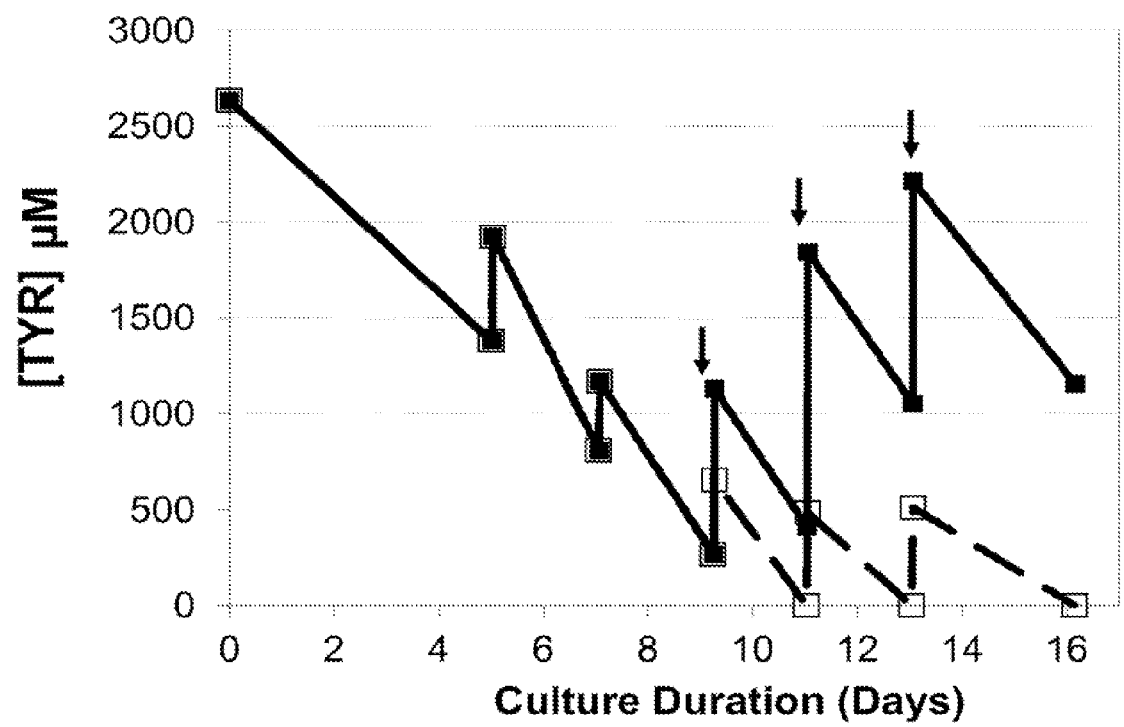
FIG. 2E is a graph showing tyrosine concentration over time.
Figure 2F:
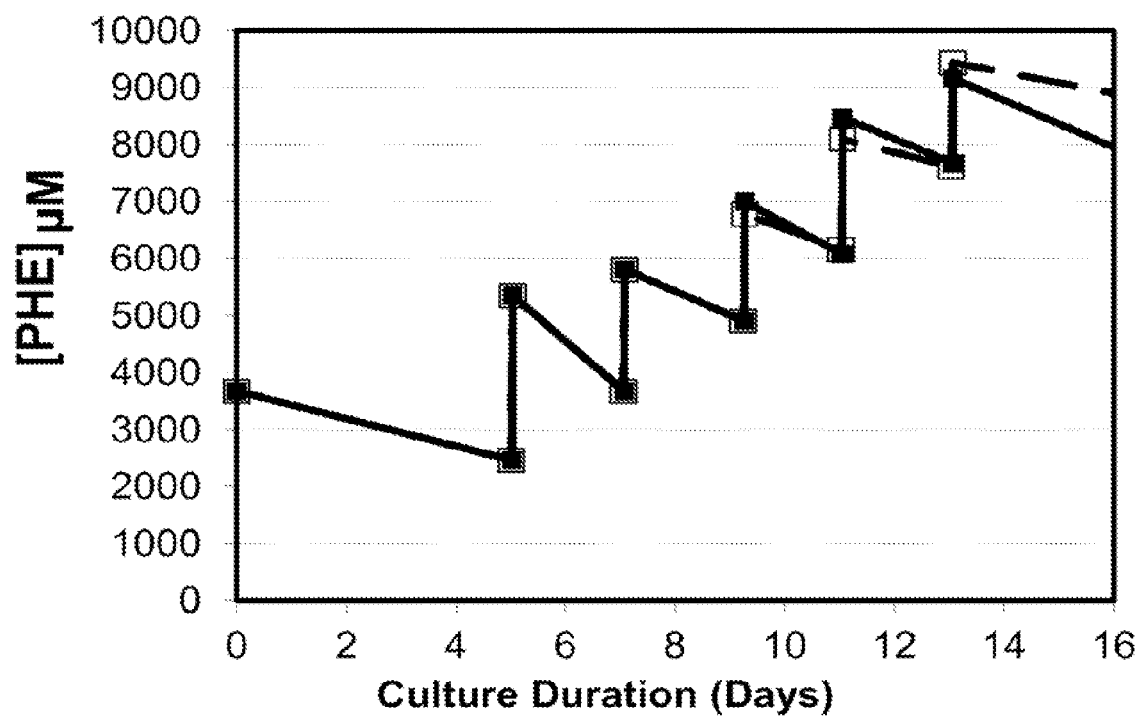
FIG. 2F is a graph showing phenylalanine concentration over time. Symbols: dashed (□) Cells provided with concentrated feed media only (control), solid (■) Cells were provided independent feeds of a concentrated feed media and a tyrosine solution (1 mM). Arrows indicate timing of tyrosine addition. Without tyrosine depletion, titer was enhanced, specific productivity maintained, viability prolonged and cell diameter increased from day 9 onwards. Phenylalanine concentration remained the same.

The culture that received the supplemental tyrosine feeds achieved a titer of 5.2 g/L in 16 days compared to 4.1 g/L observed in the control (FIG. 2A). Specific productivity was maintained, viability was prolonged and cell diameter increased as a result of the additional tyrosine. Viability was 80% on day 16 in the culture receiving the additional tyrosine compared to 60% without supplemented tyrosine and cell diameter increased from 18 μm to 20 μm respectively in the cells cultured with supplemental tyrosine (FIGS. 2B to 2D). Amino acid analysis did not show tyrosine depletion in the cultures receiving independent tyrosine feeds, indicating that these cells received sufficient levels even though tyrosine was being heavily consumed (FIG. 2E). The control culture showed tyrosine depletion and phenylalanine was not used to synthesize additional tyrosine in response to the depletion (FIG. 2F). Lactate levels were similar between the cultures; however the ammonia level was slightly decreased in the culture receiving supplemental tyrosine (data not shown).

Example 2

Another series of cultures was prepared as described above and were supplemented with independent feeds of a concentrated tyrosine feed solution at 1 mM (control), 1.5 mM, 2 mM and 4 mM (negative control) to determine an optimal tyrosine concentration in the cell culture medium. The first independent tyrosine feed was administered on day 7 rather than day 9 to maintain higher tyrosine levels earlier in the cell culture medium to avoid possible depletion. Independent tyrosine feeds were then given on subsequent feed events after day 7. Surviving cultures were carried for 28 days instead of 16 with additional independent tyrosine feeds on days 16, 18 and 21. Additional samples were taken on day 18 and daily from day 21 to 28. The amount of concentrated feed media was reduced to 7% (7 mls) provided on days 16 and 18 and 5% (5 mls) on day 21.

Figure 3A:
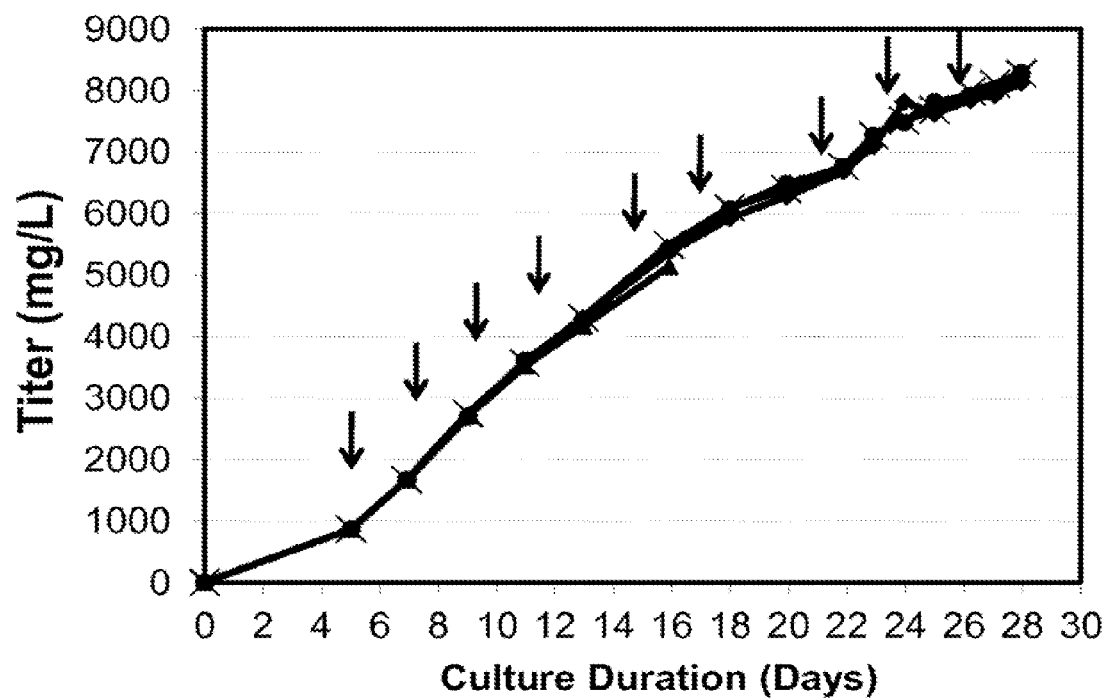
FIG. 3A is a graph showing titer over time.
Figure 3B:
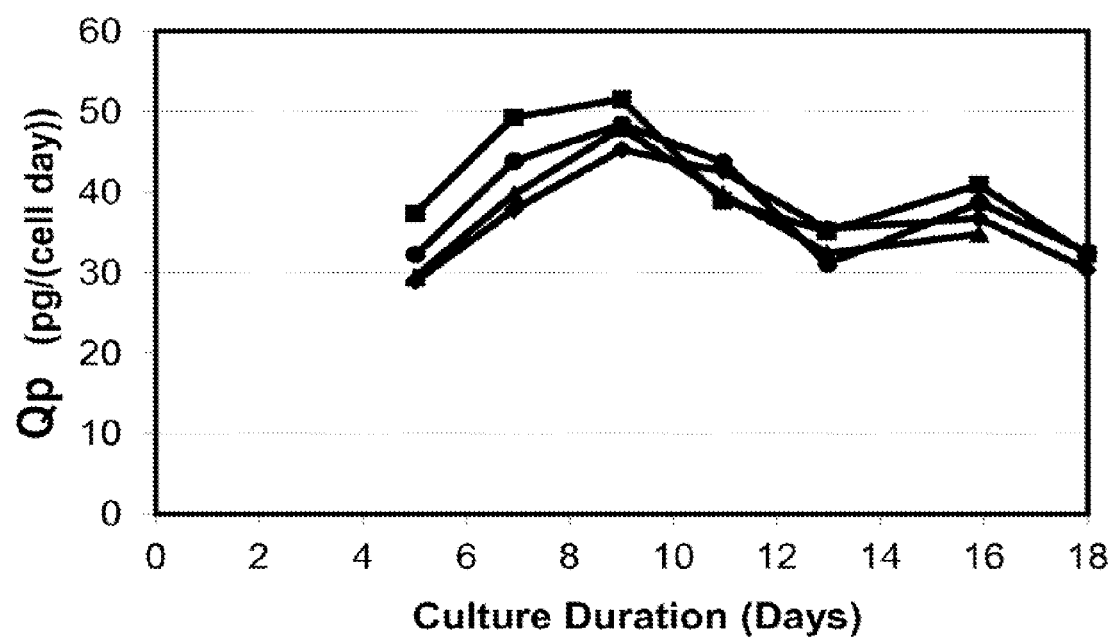
FIG. 3B is a graph showing specific productivity (Qp) over time.
Figure 3C:
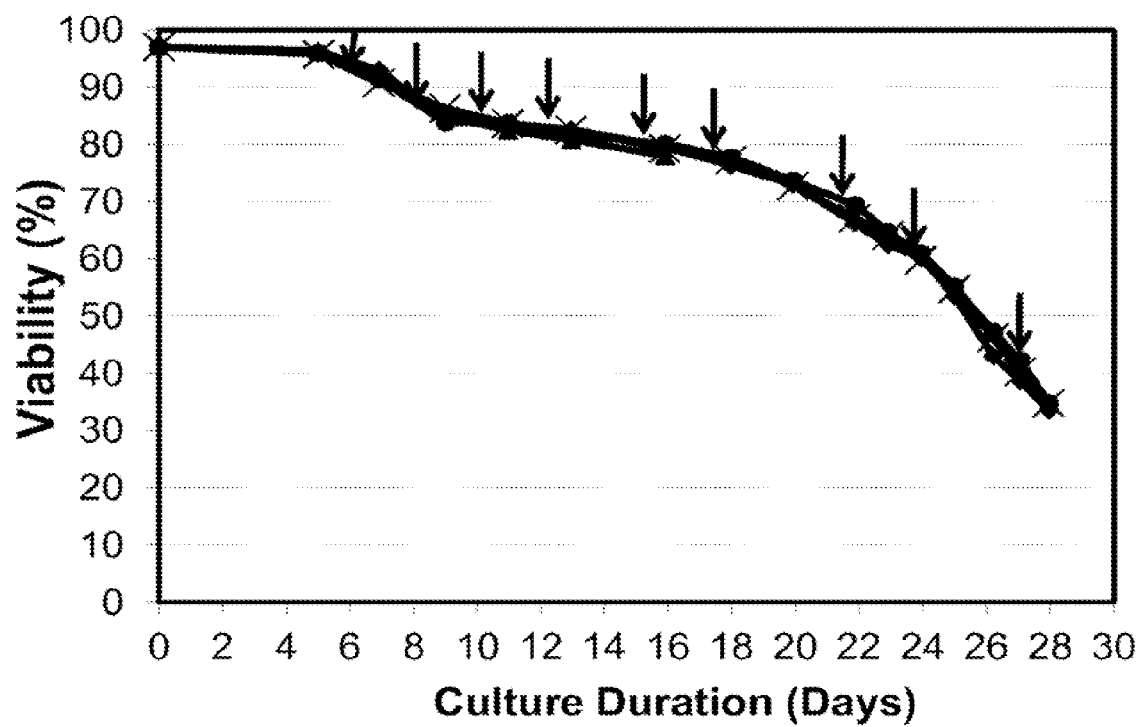
FIG. 3C is a graph showing viability over time.
Figure 3D:
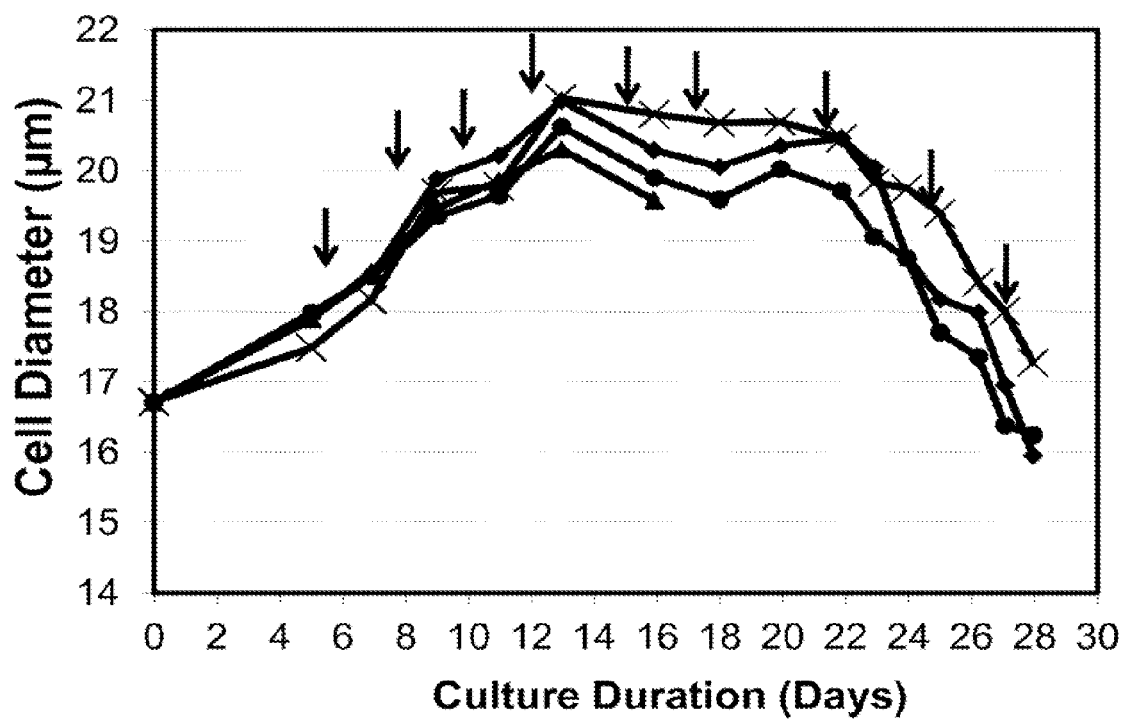
FIG. 3D is a graph showing cell diameter over time.
Figure 3E:
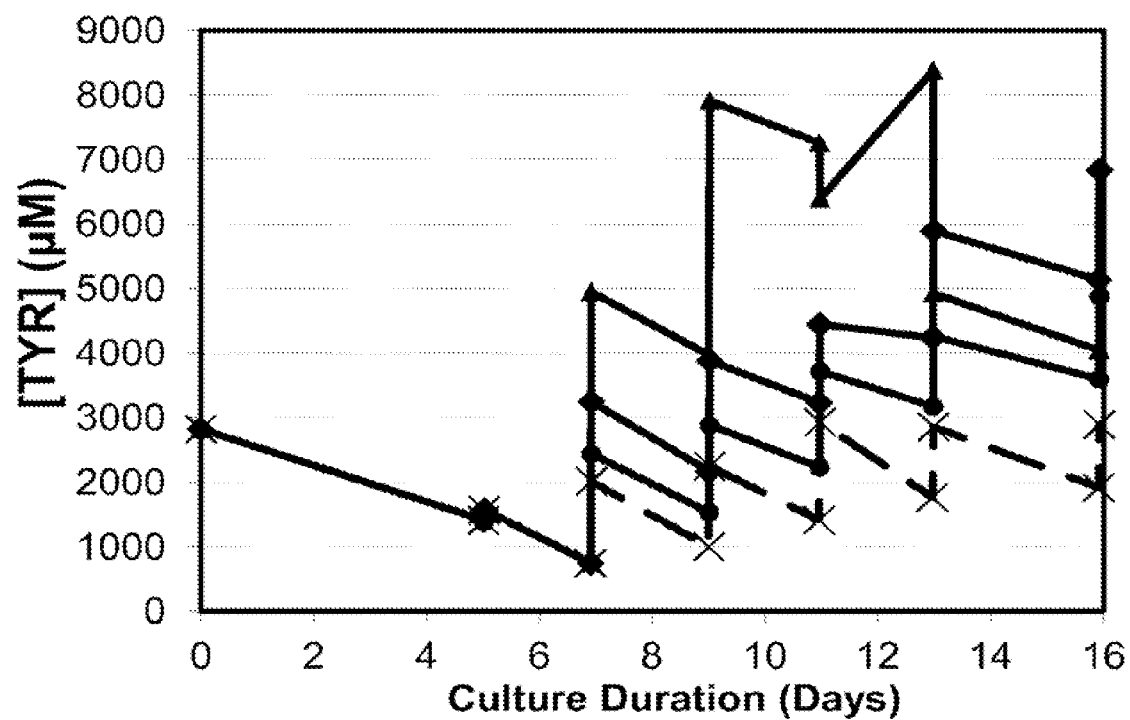
FIG. 3E is a graph showing tyrosine concentration over time.
Figure 3F:
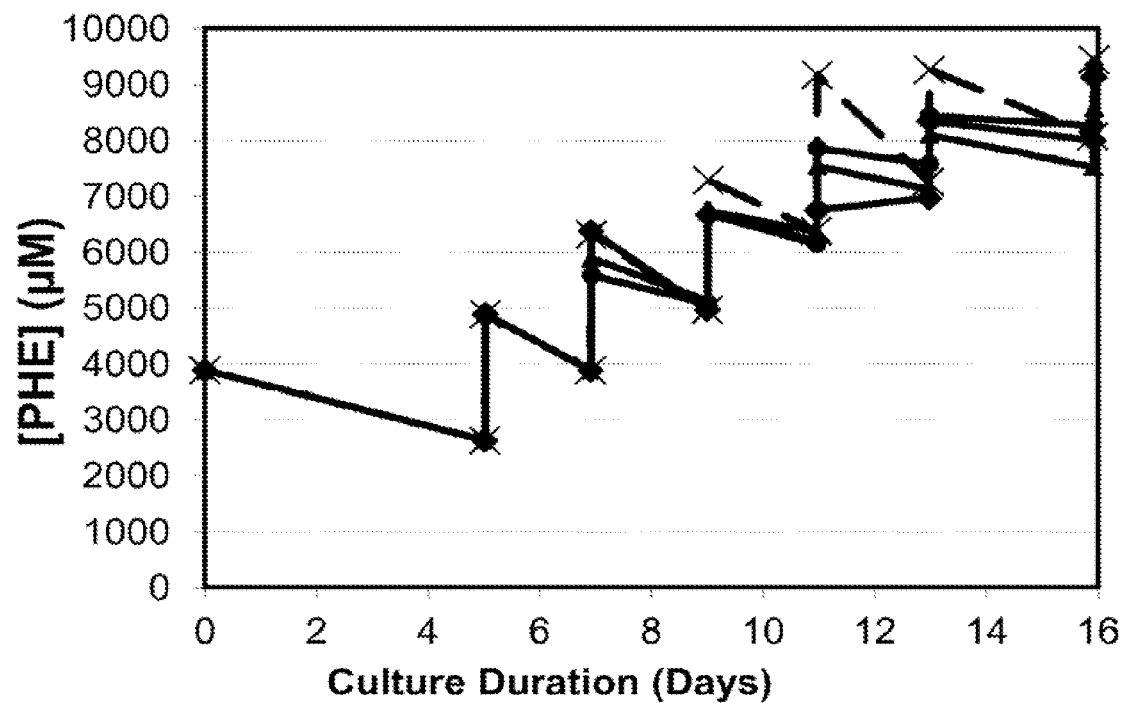
FIG. 3F is a graph showing phenylalanine concentration over time. Symbols: dashed (×) Cells provided with independent feeds of a concentrated feed media and a tyrosine solution (1 mM feed) starting on day 7 (control), solid (●) cells provided with independent feeds of a concentrated feed media and a tyrosine solution (1.5 mM feed), solid (♦) cells provided with independent feeds of a concentrated feed media and a tyrosine solution (2 mM feed), and solid (▲) cells provided with independent feeds of a concentrated feed media and a tyrosine solution (4 mM feed). Arrows indicate timing of tyrosine additions. Tyrosine concentration did not affect the phenylalanine concentration. Extension of culture duration resulted in increasingly higher titer from day 16 onwards.
Figure 4A:
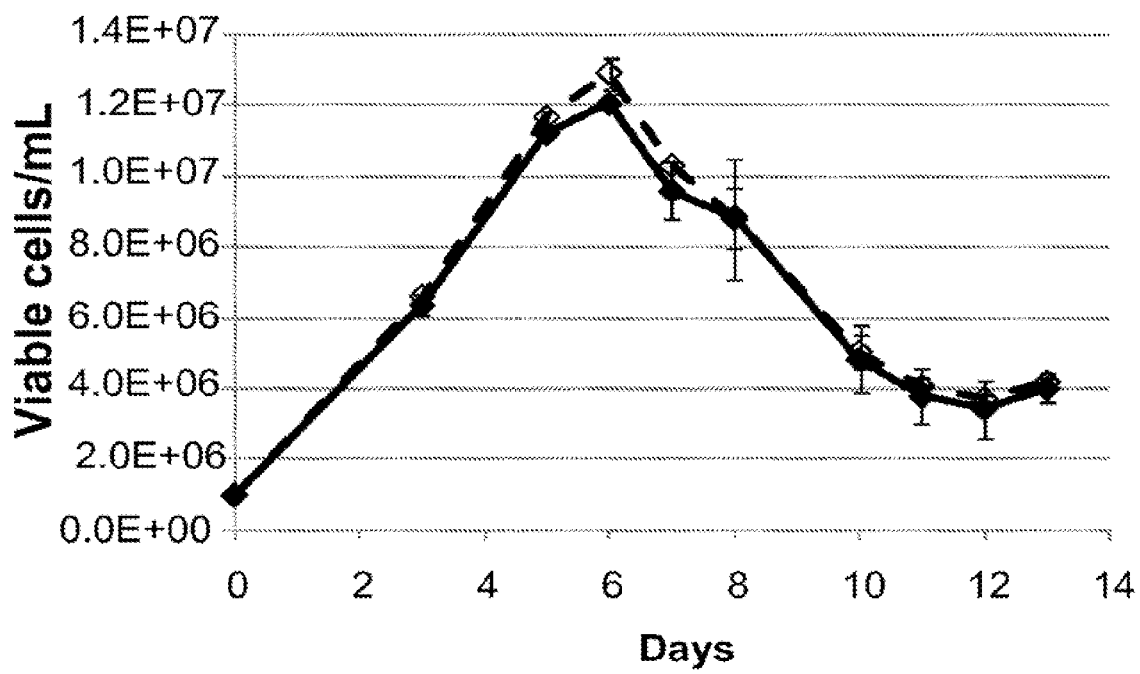
FIG. 4A is a graph showing viable cell density over time.
Figure 4B:
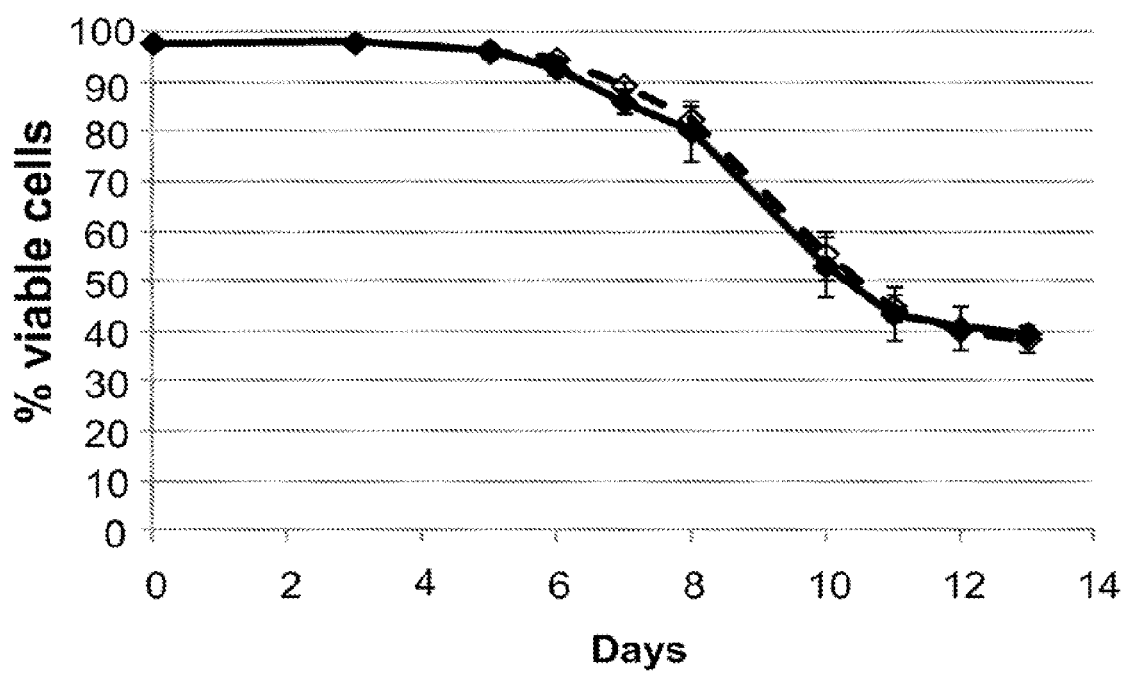
FIG. 4B is a graph showing viability over time.
Figure 4C:
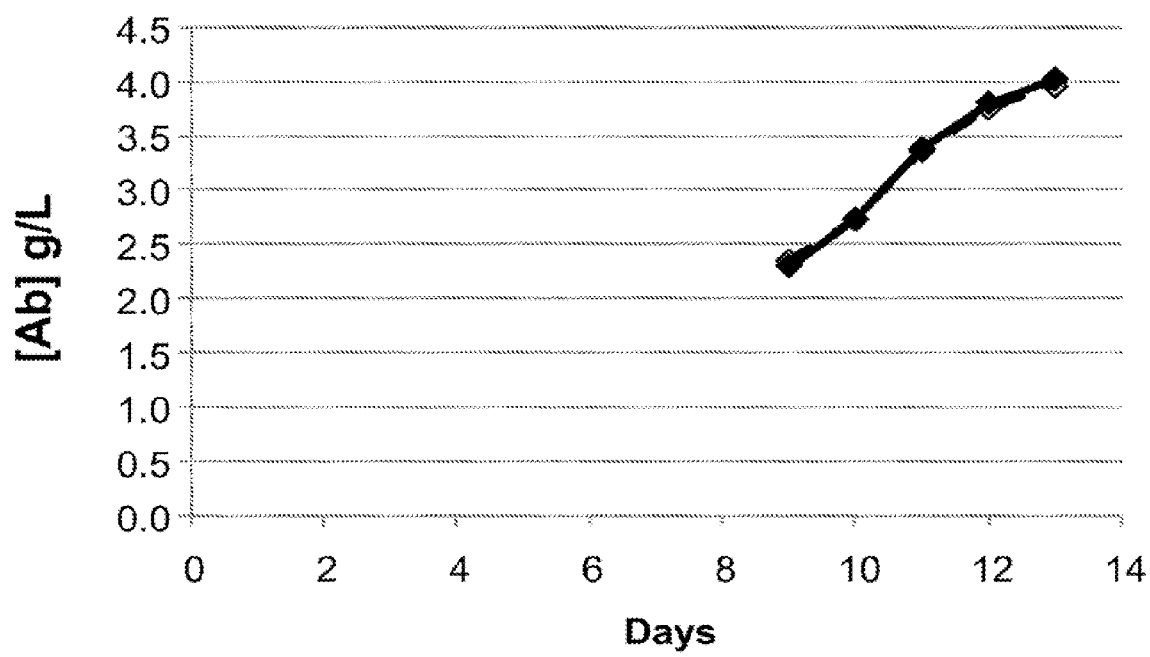
FIG. 4C is a graph showing titer over time. Symbols: solid (♦) Concentrated feed media containing cysteine but not tyrosine. Supplemented with independent tyrosine feeds. Open (◊) Concentrated feed media that does not contain cysteine or tyrosine. Supplemented with independent cysteine and independent tyrosine feeds. Growth, viability and antibody productivity were not diminished as a result of removing tyrosine and cysteine from the feed medium and delivering them as a separate concentrated feeds.
Figure 5A:
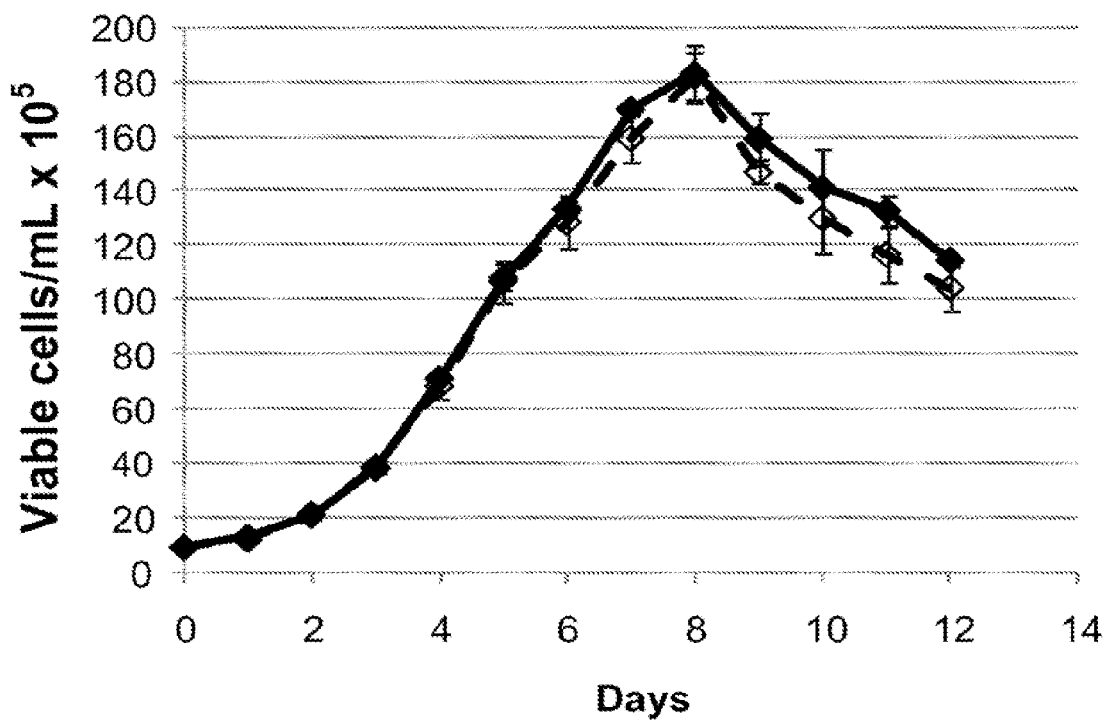
FIG. 5A is a graph showing viable cell density over time.
Figure 5B:
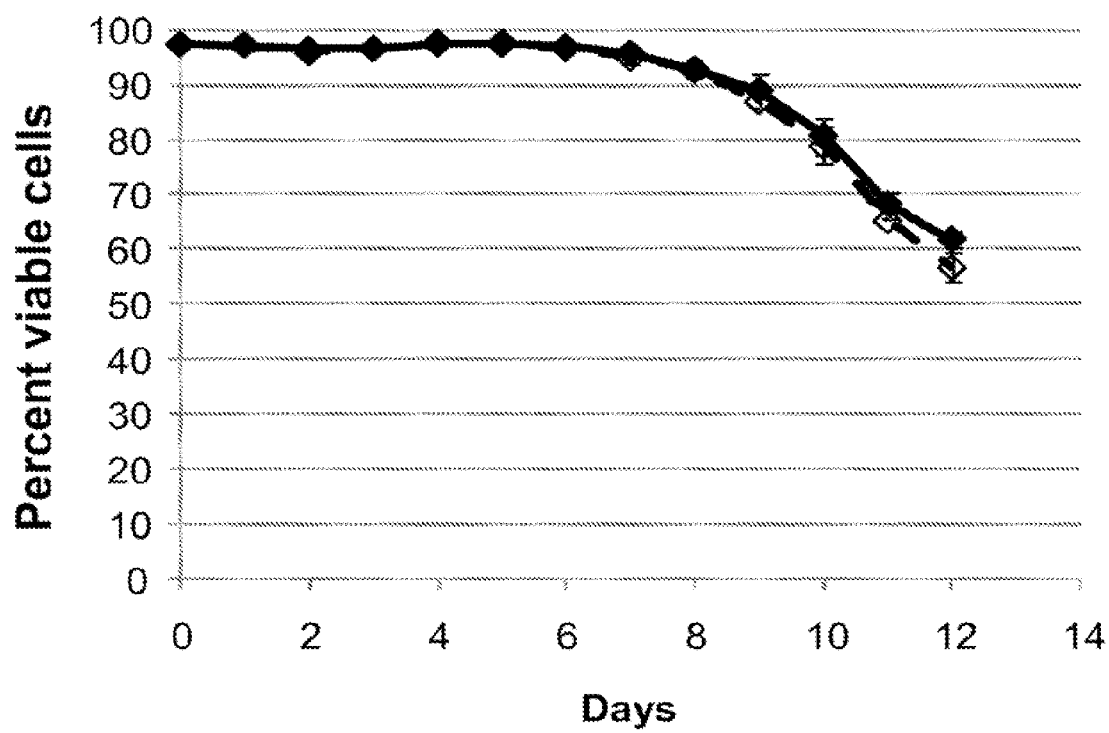
FIG. 5B is a graph showing viability over time.
Figure 5C:
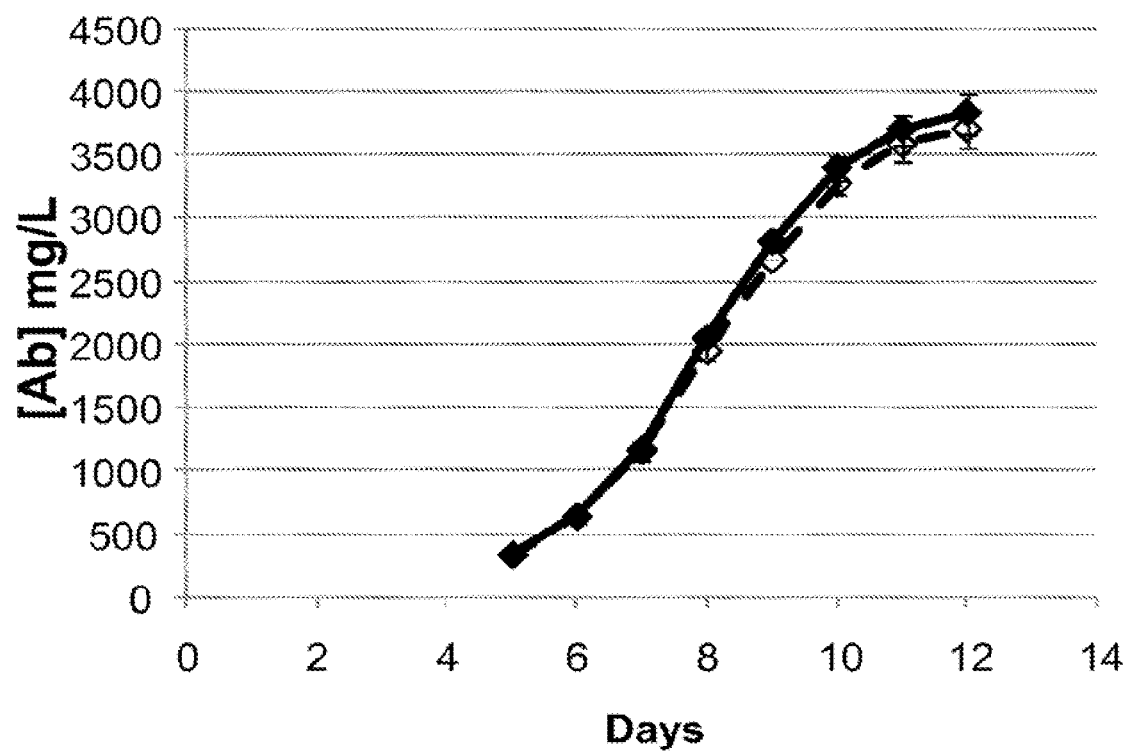
FIG. 5C is a graph showing titer over time.
Figure 5D:
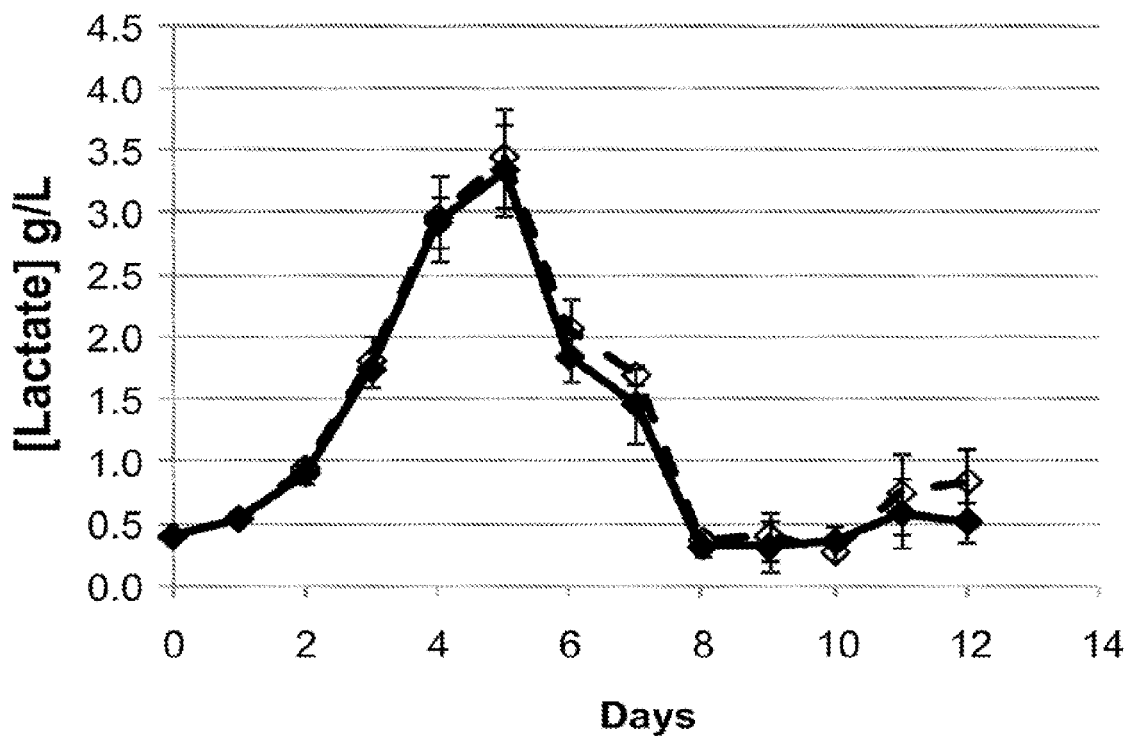
FIG. 5D is a graph showing lactate over time. In all cases the concentrated feed media did not contain tyrosine, cysteine or cystine. Symbols: solid (♦) Supplemented with independent feeds of a combined tyrosine and cystine feed solution. Open (◊) Supplemented with independent cysteine and independent tyrosine feeds. Growth, viability, antibody productivity and lactate production were not diminished as a result of removing tyrosine and cysteine from the feed medium and delivering them as a separate concentrated feeds.

Tyrosine additions targeting 1.5 mM, 2 mM and 4 mM starting on day 7 did not show any additional benefit to performance compared to the 1 mM control (FIGS. 3A to 3D). The 4 mM tyrosine feeds raised the pH as high as 7.45 but did not negatively affect VCD (data not shown), viability or titer. However, high levels of tyrosine caused the culture to form clumps that stuck to the bottom of the flask due to precipitation. Spent media analysis showed that these cultures accumulated concentrations of tyrosine of between 8 to 9 mM, and that again, phenylalanine was not utilized (FIG. 3E and 3F). For those cultures carried beyond 16 days the titer was 8.28 g/L and the Qp was maintained along with culture viability at 28 days (FIGS. 3A to 3C). Supplying extra tyrosine starting on day 7 helped maintain higher tyrosine levels earlier in the culture and avoided depletion (FIG. 3E). $NH_4^+$ levels were maintained under 8 mM when tyrosine was first added on day 7 versus 10 mM on day 9 (data not shown).

Tyrosine depletion in production phase cell cultures resulted in a rapid drop in viability, a decrease in Qp and a loss of titer even though the cultures were routinely fed with a concentrated feed medium containing a maximal amount of tyrosine. By delivering extra tyrosine using the above described independent feeding method, viability was prolonged, cell diameter increased and Qp maintained during the stationary phase of the culture resulting in significantly higher titers. The prolonged viability allowed for the extension of the culture duration which is critical for enhancing productivity.

The benefits of having non-depleted tyrosine levels in the culture are evident from the above results. However, due to tyrosine's low solubility limitation, compounding more tyrosine into the concentrated feed medium formulation was not a solution. Preparing a concentrated tyrosine feed solution and using it to provide independent additions of tyrosine to the cell culture medium was demonstrated to maintain a level of tyrosine in the cell culture medium that was not achievable using the concentrated feed medium and prevented depletion and the resulting decline in cell viability, Qp and titer without disruption of the production phase of the culture. This method is production friendly and can be readily implemented without any significant changes to a production facility.

Example 3

In this experiment, either tyrosine or tyrosine and cysteine were removed from the concentrated feed medium and provided as separate tyrosine and/or cysteine feeds.

Chinese hamster ovary (CHO) cells expressing a recombinant antibody were inoculated at $1\times10^6$ cells/mL into a defined serum-free culture medium containing 0.98 g/L tyrosine and 0.5 g/L cysteine. The cultures were maintained in 250 mL vented shake flasks with a 50 mL culture volume. The cultures were incubated at 36° C., 5% $CO_2$, 70% relative humidity, and 160 rpm on a platform having a 50 mm orbital diameter.

A 100 g/L L-tyrosine $2Na^+2H_2O$ (SAFC Biosciences, Lenexa, Kans.) concentrated tyrosine feed solution was prepared in distilled $H_2O$. A 100 g/L L-cysteine HCl (JT Baker/Avantor Performance Materials, Phillipsburg, N.J.) concentrated cysteine feed solution was prepared in distilled $H_2O$.

The culture was maintained for 13 days. Glucose was maintained at >2 g/L.

On days 3, 6, and 8, the cells were fed: (a) a concentrated defined serum-free feed medium containing cysteine and sodium pyruvate but lacking tyrosine. In addition, 0.188 mL of the 100 g/L concentrated tyrosine feed solution was provided as an independent feed. (b) a concentrated defined serum-free feed medium that lacked both tyrosine and cysteine but contained sodium pyruvate. In addition, 0.188 mL of the 100 g/L concentrated tyrosine feed solution and 0.093 mL of 100 g/L concentrated cysteine feed solution were provided as independent feeds.

Samples were collected on days 3, 5, 6, 7, 8, 10, 11, 12 and 13. On each sample day, viable cell density, viability and glucose concentration were determined Titer was determined on days 8, 10, 11, 12 and 13.

Viable cell density (VCD) and viability were determined by Guava Viacount assay (Millipore Billerica, Mass.) and metabolites (glucose) using reagent kits from Polymedco Inc. (Cortlandt Manor, N.Y.). Titer was measured by Protein A HPLC analysis using affinity chromatography where Protein A was immobilized on a column support. At neutral pH, antibody molecules were bound to the Protein A through the Fc region while host-cell proteins, conditioned media components and buffer were eluted from the column in the flow-through. Captured antibodies were eluted at acidic pH and detected by UV absorbance at 280 nm. A calibration curve was derived from an antibody standard and the corresponding peak areas using linear regression analysis. Concentrations of the antibody in the test samples were then calculated from the calibration curve. Lactate was measured using a YSI Select analyzer (YSI, Inc., Yellow Springs, Ohio).

Figure 1B:
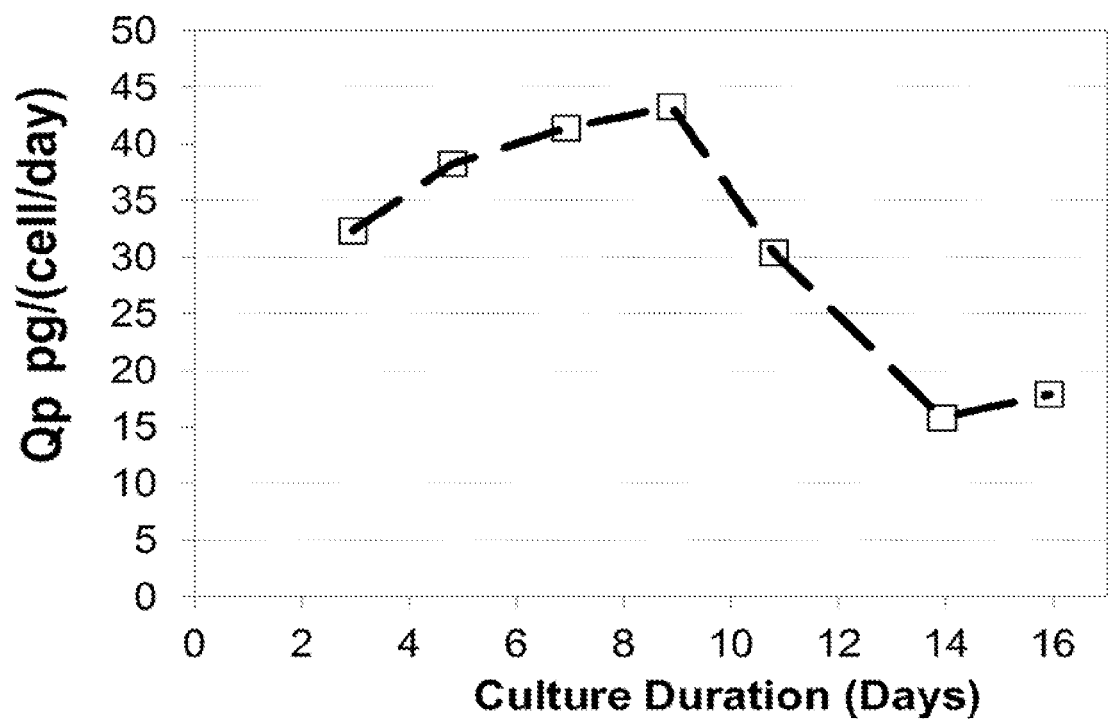
FIG. 1B is a graph showing specific productivity (Qp) over time.
Figure 1C:
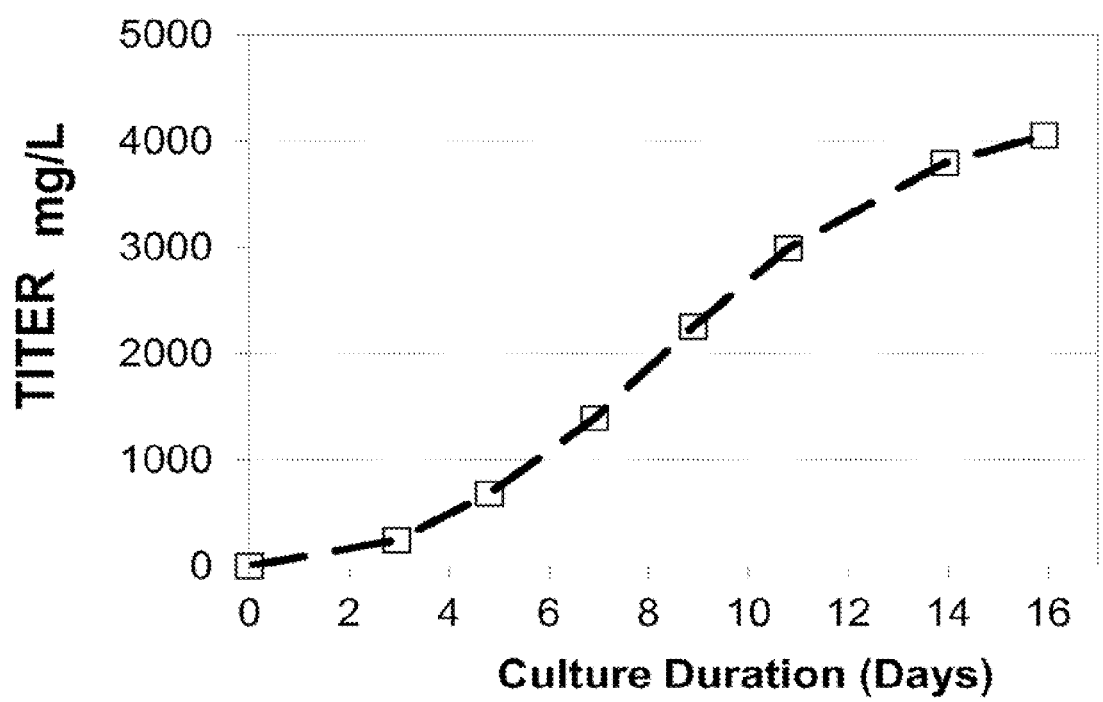
FIG. 1C is a graph showing titer over time.
Figure 1D:
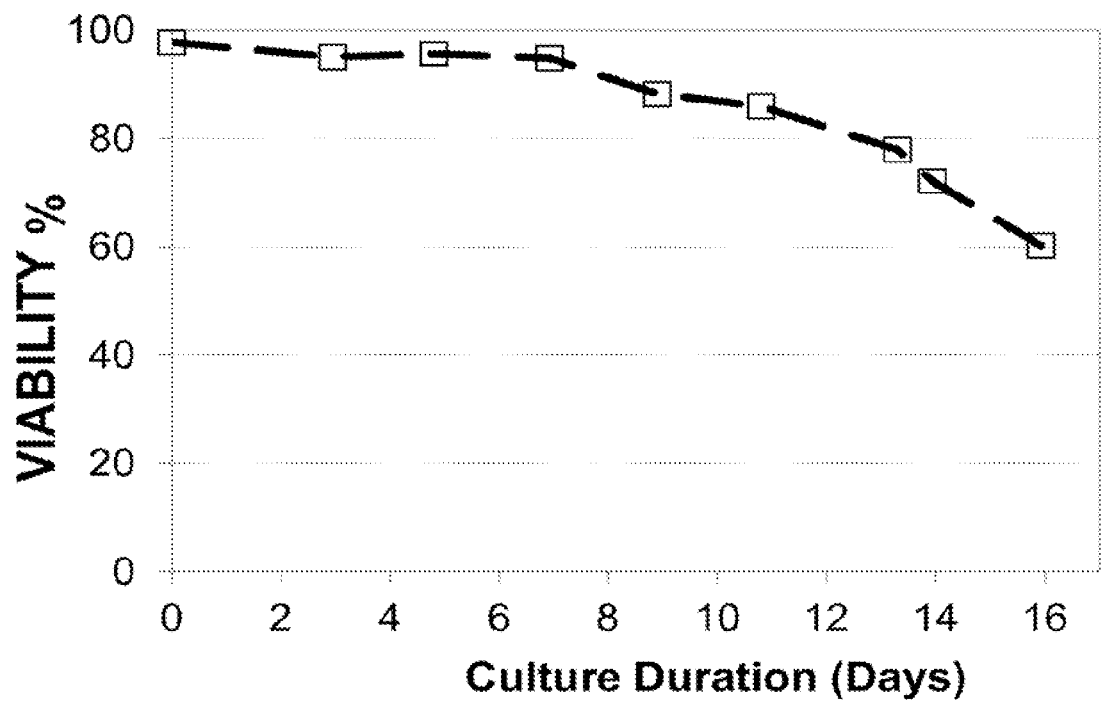
FIG. 1D is a graph showing viability over time.
Figure 1E:
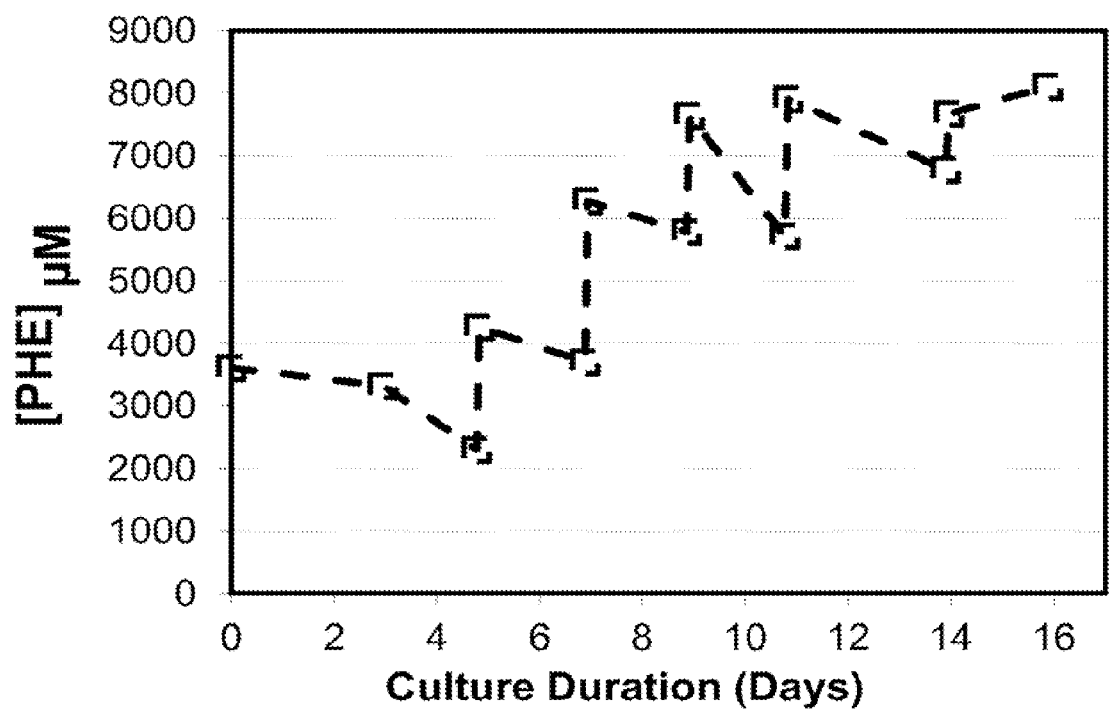
FIG. 1E is a graph showing phenylalanine concentration over time. Symbols: (□) Concentrated feed media only, no independent tyrosine feeds. Low tyrosine levels coincided with a drop in viability and Qp from day 9 onwards. Phenylalanine accumulated over time and did not convert to tyrosine after tyrosine depletion.

Growth, viability and antibody productivity were not diminished as a result of removing tyrosine and cysteine from the feed medium and delivering them as a separate concentrated feeds (FIG. 1A-C).

Example 4

It is desirable from a process operations perspective to keep the number of feed steps to a minimum. Combining the concentrated cysteine and tyrosine feeds into a single concentrated feed solution would minimize the number of feed steps while maintaining the desirable flexibility of independent tyrosine and cysteine feeds. However, cysteine in its reduced form is not soluble with tyrosine due to the high pH of the tyrosine solution. To overcome this incompatibility, the oxidized form, cystine, was used. Cystine and tyrosine are both readily soluble at pH >8 and solubility is high at pH >10. Both cystine and tyrosine can be dissolved in a sodium hydroxide solution (for example 0.1N NaOH) and the resulting solution has the added benefit of not requiring subsequent viral inactivating treatments such as pasteurization or viral filtration.

A comparison was made of independent tyrosine and cysteine feeds with an independent feed of a combined tyrosine and cystine stock.

CHO cells expressing a recombinant antibody were inoculated at $9 \times 10^5$ cells/mL into a defined serum-free culture medium containing 0.98 g/L tyrosine and 0.5 g/L cysteine. The cultures were maintained in 1 L bioreactors with an 800 mL initial working volume. Temperature was maintained at 36° C., agitation rate was 290 rpm, dissolved oxygen was maintained at 30% by sparging, pH was maintained at 7.0 and was controlled by CO2 and sodium carbonate addition as required. Glucose was maintained at >2 g/L.

In addition to the concentrated tyrosine and cysteine feed solutions described above, a 100 g/L L-tyrosine $2Na^+2H_2O$ (SAFC Bioscience), 33.5 g/L L-cystine (Sigma-Aldrich), 0.1N NaOH (JT Baker/Avantor Performance Materials) feed solution was prepared.

On days 3, 6, and 8, the cells were fed: (a) a concentrated defined serum-free feed medium lacking tyrosine and cysteine. In addition, 1.9 mL of the 100 g/L concentrated cysteine feed solution and 3.9 mL of the 100 g/L concentrated tyrosine feed solution were provided as independent feeds. (b) the same concentrated defined serum-free feed medium lacking tyrosine and cysteine. In addition, 3.9 mL of the 33.5 g/L cystine and 100 g/L tyrosine concentrated feed solution was provided as an independent feed.

Feeding a concentrated cysteine feed solution and a concentrated tyrosine feed solution separately or feeding a combined concentrated cystine and tyrosine feed solution resulted in equivalent cell culture performance; therefore, the two nutrients can be combined into a single independent feed solution to simplify the feed operations without diminishing the performance of the culture (FIG. 2A-D).

What is claimed is:

1. A method of culturing Chinese Hamster Ovary (CHO) cells expressing a recombinant protein, comprising growing the CHO cells in a defined serum-free culture medium during a growth phase and maintaining the CHO cells in the cell culture medium during a production phase by supplementing the cell culture with a concentrated serum-free defined feed medium containing tyrosine and further supplementing the cell culture with one or more independent tyrosine feeds, wherein the independent tyrosine feed provides at least about 1 mM to at least about 2 mM tyrosine at each feed, wherein viability was prolonged, specific productivity was maintained, and titer was improved compared to CHO cells not receiving independent tyrosine feeds.

2. The method according to claim 1, wherein the independent tyrosine feed provides at least about 1 mM tyrosine.

3. The method according to claim 2, wherein the independent tyrosine feed provides at least about 1.38 mM tyrosine.

4. The method according to claim 1, wherein the concentration of tyrosine in the cell culture medium does not exceed 8 mM.

5. The method according to claim 1, wherein the independent tyrosine feed begins at least by day 5 of the production phase.

6. The method according to claim 1, wherein the independent tyrosine feed begins on day 3 of the production phase.

7. The method according to claim 1, wherein the independent tyrosine feeds begin on day 7.

8. The method according to claim 1, wherein the independent tyrosine feed begins prior to the production phase.

9. The method according to claim 1, wherein the independent tyrosine feed is made concurrently with the feed of the concentrated serum-free defined feed medium.

10. The method according to claim 1, wherein the independent tyrosine feed is not concurrent with the feed of the concentrated serum-free defined feed medium.

11. The method according to claim 1, wherein the recombinant protein is selected from the group consisting of a human antibody, a humanized antibody, a chimeric antibody, a recombinant fusion protein, or a cytokine.

* * * * *